United States Patent [19]

Bales, Jr.

[11] Patent Number: 5,049,124

[45] Date of Patent: Sep. 17, 1991

[54] CATHETER DRIVE APPARATUS HAVING FLUID DELIVERY BEARING

[75] Inventor: Thomas O. Bales, Jr., Coral Gables, Fla.

[73] Assignee: Dow Corning Wright Corporation, Arlington, Tenn.

[21] Appl. No.: 677,603

[22] Filed: Mar. 27, 1991

Related U.S. Application Data

[63] Continuation of Ser. No. 417,022, Oct. 14, 1989, abandoned.

[51] Int. Cl.⁵ .............................................. A61B 17/32
[52] U.S. Cl. ...................................... 604/22; 606/159
[58] Field of Search .................. 604/22; 606/159, 170, 606/180, 128

[56] References Cited

U.S. PATENT DOCUMENTS 4,631,052 12/1986 Kensey .
4,664,112 5/1987 Kensey et al. .
4,681,106 7/1987 Kensey et al. .
4,681,561 7/1987 Hood et al. .
4,686,982 8/1987 Nash .
4,690,140 9/1987 Mecca ............................... 604/22 X
4,747,406 5/1988 Nash .
4,747,821 5/1988 Kensey et al. .
4,749,376 6/1988 Kensey et al. .
4,790,813 12/1988 Kensey et al. .
4,795,438 1/1989 Kensey et al. .

Primary Examiner—Michael H. Thaler
Attorney, Agent, or Firm—Watts, Hoffmann, Fisher & Heinke Co.

[57] ABSTRACT

A catheter having a distal working head carried by a tubular sheath. A bearing fixed to the tubular sheath forms fluid delivery passageways in fluid communications with the center of the sheath. The fluid delivery passageways open into a vessel via radially extending ports that open out into the vessel through an end face of the bearing.

8 Claims, 1 Drawing Sheet

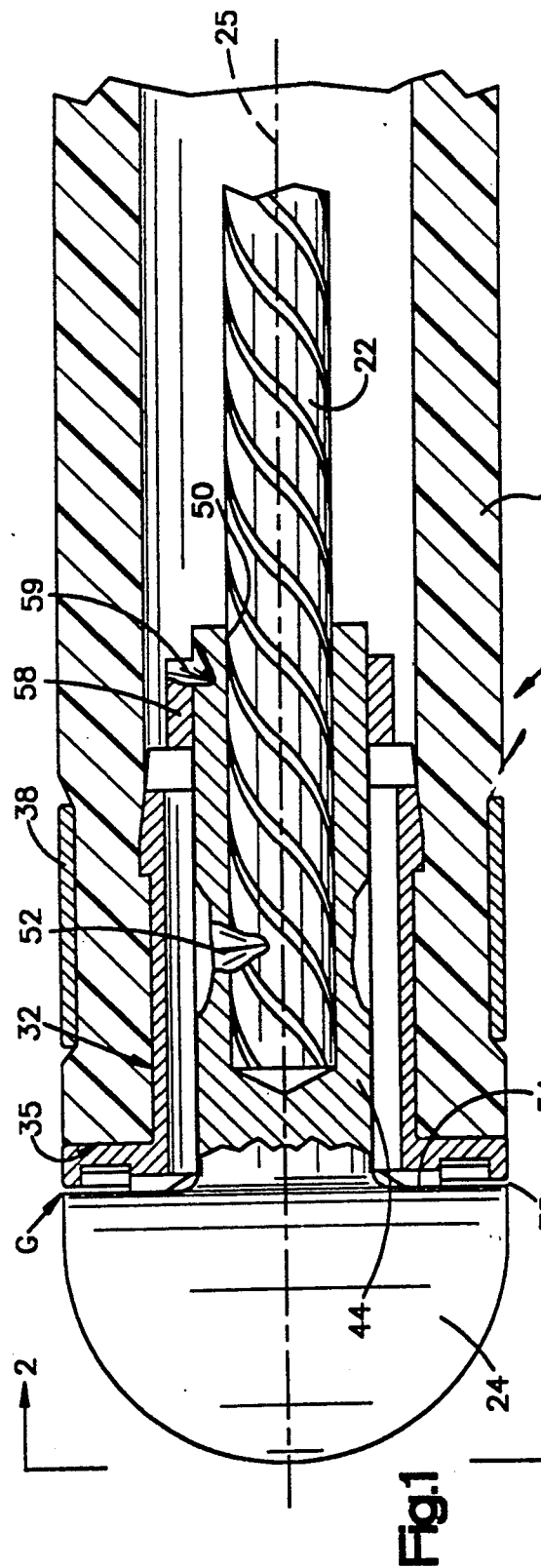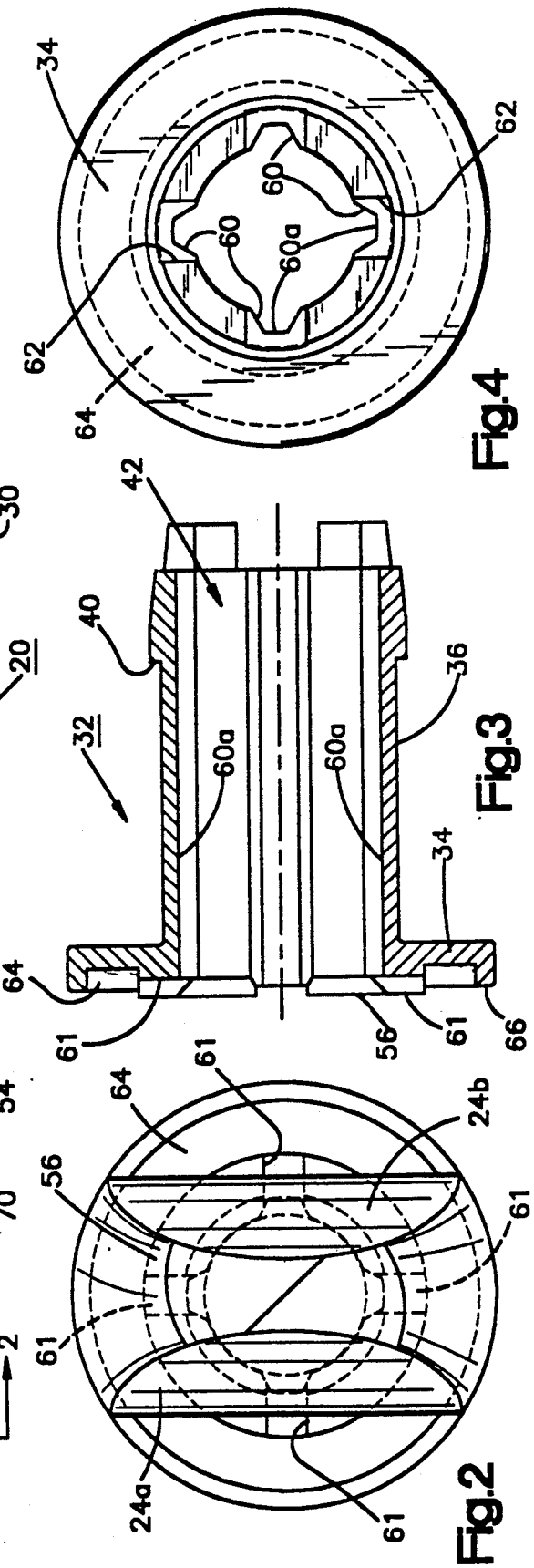

CATHETER DRIVE APPARATUS HAVING FLUID DELIVERY BEARING

This is a continuation of copending application Ser. No. 07/417,022 filed on Oct. 4, 1989, now abandoned.

TECHNICAL FIELD

The present invention relates to a catheter having a rotatable working head for abrading deposits within a subject vessel such as a totally or partially occluded blood vessel.

BACKGROUND ART

Due to a mechanism not entirely understood by physicians the cardiovascular blood delivery system often becomes less efficient as one ages. Although the causes of arteriosclerosis are not completely understood, one symptom is the partial or, in extreme cases, the total blockage of a blood vessel due to a build up of deposits along an inner surface of the blood vessel.

Prior art proposals recognize that one possible procedure for treating a condition of partially or totally blocked blood vessels is to open the blocked blood vessel. One such prior art technique for reopening a blocked blood vessel is to insert a balloon catheter within the vessel to expand the vessel and either break loose deposits within the vessel or alternatively, increase the size of the lumen passing through those deposits.

An alternate proposal for opening a blocked vessel is to bring a high-speed rotating device into contact with occluded portions of the blood vessel. The rotating device produces cutting, abrading, or fluid turbulence to open the vessel and increase blood flow. One device for physically opening the blood vessel in this manner is disclosed in U.S. Pat. No. 3,762,416 to Moss entitled "Improvements In or Relating To Drills for Clearing Obstructions". In this patent, a high-speed motor rotates a flexible drive shaft connected to a cutting bit. The bit and flexible drive shaft are inserted into an occluded blood vessel so that when the bit is rotated at high speed and moved into contact with occluded regions it breaks loose deposits within the blood vessel.

A more recent prior art patent disclosing a similar system for blood vessel cannulization is disclosed in U.S. Pat. No. 4,445,509 to Auth entitled "Method and Apparatus for Removal of Enclosed Abnormal Deposits". This patent describes a differential cutting tool inserted into an occluded blood vessel. Again, high speed rotation of the cutting tool causes the tool to remove abnormal deposits from inside the blood vessel.

U.S. Pat. No. 4,589,412 to Kensey entitled "Method and Apparatus for Surgically Removing Remote Deposits" discloses a procedure for removing atherosclerotic plaque. A cutting tip is rotated by the application of fluid pressure through a multi-lumen catheter. U.S. Pat. No. 4,747,821 to Kensey et al, which issued May 31, 1988 also discloses a catheter that includes a rotating cutting head at its distal end.

At the distal end of the catheter disclosed in the '821 patent a specially configured rotatable cutting tip is supported within a bearing fixed to the flexible catheter and having axially extending grooves which provide a fluid communication path from the center passageway of the catheter to the subject blood vessel. As the rotatable cutting tip of the '821 catheter rotates, these grooves are periodically exposed. Fluid passing down the interior region of the catheter under pressure exits the catheter via these grooves and in this way, an opaque dye can be injected into the blood vessel, thereby allowing an attending physician to monitor progress of the cutting tip as it is rotated.

Experience with a catheter similar to that depicted in the '821 patent to Kensey et al indicates that when boring through fatty or fibrous tissue, tissue that is partially or totally separated from the vessel can enter the longitudinal or axially extending grooves in the bearing that rotatably supports the cutting tip. This not only clogs the passage of fluid from the center region of the catheter, but can also cause the material to wind around the cutting head. This causes the catheter to bind and in some instances can even cause the flexible drive shaft to break. The physician conducting the procedure must then withdraw the catheter from the subject even though the vessel may not be adequately treated. Additionally, if tissue becomes wound around the cutting tool, but remains attached to the vessel wall it may pull on the interior wall linings of the vessel and seriously damage the vessel.

DISCLOSURE OF THE INVENTION

The present invention concerns a catheter having a rotatable working head supported by a new and improved bearing. The bearing provides a fluid flow path between a vessel that is being treated and a center region of the catheter. This is accomplished in a manner less prone to clogging by material dislodged from the vessel wall.

In accordance with the invention, the catheter includes an elongated flexible sheath having a center passageway and having a length which extends from outside a subject to a region of interest within a subject vessel. An abrasive, rotatable working head is driven by a drive member which extends through the sheath's center passageway to apply a motive power to the working head. A bearing is interposed between the flexible sheath and the rotating working head. The bearing has a bearing body that abuts a distal end of the flexible sheath and defines an outwardly facing bearing surface. One or more fluid delivery passageways are in fluid communication with the center passageway of the flexible sheath and follow a winding or tortuous path through the bearing body to open outwardly into the subject vessel. By defining a tortuous path, the fluid delivery passageways in the bearing body tend to impede entry of fibrous tissue as the tissue becomes dislodged or separated from the vessel wall.

In the preferred and disclosed design, the bearing includes a shaft portion which enters the distal tip of the flexible sheath and defines a through passageway to accommodate the rotatable working head. Axially extending grooves similar to those depicted in the '821 patent to Kensey et al extend along an inner surface of the bearing shaft to allow fluid to pass through the bearing to the vessel. Rather than open directly into the vessel as disclosed in the '821 patent, however, a bearing constructed in accordance with the present invention includes one or more radially extending ports defined by the bearing surface which are covered by the rotatable working head and which open into the vessel. As the working head rotates the one or more radially extending ports are exposed to the vessel and define a fluid passageway from the center passageway of the flexible sheath to the interior of the vessel.

A preferred embodiment of the present invention is described in more detail in conjunction with the accompanying drawings.

BRIEF DESCRIPTION OF THE DRAWINGS

FIG. 1 is a partially sectioned view of a distal end of a catheter constructed in accordance with the present invention;

FIG. 2 is a view as seen from the plane defined by the line 2—2 in FIG. 1;

FIG. 3 is a sectioned view of a bearing that supports a distally located rotating working head; and FIG. 4 is an end elevation view of the bearing depicted in FIG. 3.

BEST MODE FOR CARRYING OUT THE INVENTION

Referring now in greater detail to the various figures of the drawings wherein like reference characters refer to like parts, there is shown in FIG. 1 the distal end of a catheter 20 for intravascular or other surgical applications. The catheter 20 is an elongated member including a flexible drive shaft 22 (only a portion of which can be seen in FIG. 1) located therein.

Located at the distal end portion of the catheter 20 is a working head or tool 24. The working head is arranged to be moved at a high speed with respect to the catheter by the drive shaft to effect the surgical procedure to be carried out by the catheter. The proximal end of the drive shaft is located outside the patient's body and is connected to a source of rotary power, e.g., an electric motor (not shown). In the preferred embodiment disclosed herein, the drive means 22 effects the rotary movement of the working head 24 under the power provided from the remote power source (motor).

When the catheter 20 is used for treating occlusive atherosclerotic disease, such as opening a restriction in an artery formed by atherosclerotic plaque, the catheter is introduced into the vascular system of the patient such as through an opening in the femoral artery at a point in the groin. The catheter is then guided through the vascular system of the patient to the site of the vascular occlusion or blockage that has been determined to exist so that its working head 24 is located immediately adjacent the restriction.

As will be recognized by those skilled in the art, such arterial restrictions are formed by the deposit of atherosclerotic plaque or some other material(s), such as waxy and/or calcified atheroma, thickened and/or ulcerated intima. Once in position, the catheter 20 is arranged to transluminally recanalize the diseased artery by dilating the stenotic or occluded area (which may or may not be covered by fibrous plaque) and/or selectively removing calcified thrombotic, or fatty tissue unprotected by fibrous plaque while allowing the artery wall to remain in241 tact.

The catheter 20 includes an elongated, flexible tubular member or jacket 30 which is formed of a suitable material, e.g., plastic, and which has a outside diameter that is small enough that the catheter 20 can be routed through the blood vessel to the region needing treatment. Representative sizes of the catheter's outside diameter are 2.7 mm (8 French), 1.7 mm (5 French), or less. These sizes are merely exemplary. Thus, in accordance with this invention, the catheter can be constructed as small as 2 French (0.67 mm).

At the distal end of the catheter 20 there is secured a sleeve-like metal bearing 32 (FIG. 3). The bearing includes a flanged distal end 34 that abuts a distal end 35 of the catheter's jacket 30 and an annular or tubular portion 36. The outside diameter of the bearing's tubular portion 36 is approximately that of the inside diameter of the catheter's jacket 30 so that it is snugly fit therein. The bearing is held firmly in place by a retaining band 38 which tightly encircles the periphery of the catheter jacket 30. A gripping edge 40 which extends about the periphery of the tubular portion 36 digs into the interior surface of the catheter jacket 30 and hold the bearing tightly in place. The bearing 32 also includes a through bore 42 (FIG. 3) extending therethrough and aligned with a longitudinal central axis 25 of the catheter.

The working head 24 includes a mounting shank or axle 44 projecting proximally and passing through the bore 42 in the bearing 32. The drive shaft is constructed from a multistrand drive cable. The drive shaft extends through the catheter's jacket 30 coaxial with axis 25 and terminates and is disposed within a longitudinal extending bore 50 in the shank 44 of the working head 24. The end of the drive shaft 22 is secured in place in the bore 50 via a laser weld joint 52.

The working head includes a generally planar rear surface 54 which rotates next to a front surface 56 of the bearing flange 34. The working head 24 is prevented from axial movement within the bearing 32 by virtue of a retaining ring 58 mounted on the proximal end of the working head axle 44 contiguous with the proximal end of the bearing. The retaining ring 58 is secured to the proximal end of the working head axle 44 via another laser weld 59.

The drive shaft 22 is supported in the central position along axis 25 by means of a spiral bearing (not shown). The bearing comprises a helical or spiral cylindrical coil of wire surrounding the multistrand drive cable. The spiral bearing extends substantially the entire length of the catheter from a proximately located point adjacent the drive motor (not shown) to the distal end of the catheter. The outer diameter of the helical bearing coil is sufficiently great so that its loops just clear the interior surface of the catheter's jacket 30 to hold the bearing securely in place therein. An inside diameter of a central passageway extending down the length of the helically coiled bearing is slightly greater than the outside diameter of the drive shaft 22 so that the drive shaft can freely rotate therein. With such a construction, the drive shaft 22 can be rotated at a high rate of speed, e.g., from 10,000 to 200,000 rpm, while the catheter is bent through a small radius of curvature, e.g., 0.75 inches (1.9 cm).

The bearing 36, the inner surface of the catheter tube 30, and the outer surface of the drive shaft 22 form a passageway through which a fluid can flow from the proximal end of the catheter to the distal end. A liquid can be expelled at the rotating working head, for example, to aid in the dilation of the arterial tissue at the working head. Moreover, a liquid can be passed down the catheter which is oxygenated to eliminate distal ischemia during the restriction opening procedure by the catheter. Also, if desired, nitrates, contrast media, or other drugs can be delivered as needed during the procedure.

The mechanism for routing a fluid from the catheter's proximal end to its distal end is described with reference to FIGS. 2-4. As can be seen in those figures, extending down the central bore 42 of the bearing's tubular portion are four, equally spaced, axial grooves 60 that extend through the bearing to the front surface 56. As seen from the proximal end of the bearing (FIG. 4) the grooves 60 have a generally trapezoidal shape, i.e., they are wider at the radius of the passageway 42 than at a base or radially outermost groove wall 60a. The grooves 60 are in fluid communication with four radially directed fluid exit ports 61 formed in the end flange 34 of the bearing 32. The proximal end of the grooves 60 terminate in radially extending, relief grooves 62. Fluid passing down the interior of catheter flows under pressure into the relief grooves 62, through the associated longitudinal grooves 60 to the ports 61.

The radially directed exit ports 61 are formed by machined grooves or depressions equally spaced about the center axis 25 that are formed in the face 56 of the bearing 32. The working head 24 covers the distal end of the grooves 60 to help inhibit material separated from the vessel from entering the grooves 60.

The working head 24 defines a convex shaped tip of a generally hemispherical shape and having a pair of generally planar diametrically disposed side faces 24a and 24b. Further details concerning the operation of the disclosed working head 24 are disclosed in issued U.S. Pat. No. 4,747,821 to Kensey et al which is incorporated herein by reference. As the working head 24 rotates within the bearing, it covers two diametrically opposite exit ports 61 (FIG. 2) while exposing portions of two other ports to the vessel interior. Each of the ports 61 extend outwardly to a circumferential circular groove 64 which extends into an outer face of the bearing flange slightly further than the depth of the ports 61.

As fluid from the proximal end of the catheter passes through the bearing 32 it moves radially outward through the ports 61. Some of the fluid escapes axially as the working head rotates and the rest reaches the circular groove 64. As seen in FIG. 2, significant portions of the groove 64 (approximately 50%) are exposed as the working head 24 rotates relative the bearing 32. This exposed groove therefore allows relatively unrestricted fluid flow from the ports 61.

As seem most clearly in FIG. 1 an outmost lip or ridge 66 of the flanged end portion 34 is not co-planar with the surface 56. This creates a small gap G between the lip 66 and the rear surface 54 of the working head 24. As also seen in FIG. 1 an edge at the interface between the rear surface 54 and the exposed face of the working head forms a sharp transition rather than the rounded transition depicted in the '821 patent to Kensey et al. This sharp edge 70 also tends to prevent material separated from the vessel from entering the bearing 32. Even though the groove 64 is exposed as the working head rotates, material separated from the vessel must traverse a winding or tortuous path (through the ports 61) to enter the grooves 60 and furthermore the sharp edge 70 tends to cut the materials into smaller pieces before it can enter the exit ports 61.

While the present invention has been described with a degree of particularity, it is the intent that the invention encompass modifications and alterations from the disclosed design falling within the spirit or scope of the appended claims.

I claim:
1. A catheter for treating a subject vessel comprising:
 a) an elongated flexible sheath having a center passageway and a length sufficient to extend from outside the subject to a treatment region within the subject vessel;
 b) a rotatable working head supported at a distal end of said sheath for abrasively treating interior walls of the vessel as the working head rotates with respect to the sheath;
 c) a drive shaft extending through the center passageway in the sheath and connected to the working head for transmitting motive power from outside the subject to the working head to effect rotation of the working head; and
 d) a bearing carried by a distal portion of the sheath for rotatably supporting the working head and defining one or more tortuous fluid flow paths between the vessel and the center passageway of the elongated flexible sheath; said bearing having an annular bearing body defining a center bore to accommodate a portion of the rotatable working head and having a flanged end portion which defines a distally facing bearing end surface; said bearing body defining one or more tortuous fluid delivery passageways each of which comprises:
  i) an axially extending passageway that opens into the center passageway of the elongated flexible sheath and
  ii) a corresponding radially extending passageway that extends radially outward from the axially extending passageway through the bearing body and opens into the vessel via a port in the bearing end surface that is at least partially exposed as the working head rotates; said port being located radially inwardly from the radial outer edge of said flanged end portion; said bearing supporting the working head in a position to simultaneously completely cover all of the axially extending passageways of the one or more tortuous fluid delivery passageways as said working head rotates.

2. The catheter of claim 1 wherein the flanged portion of the bearing defines a circular groove radially outward of the radial passageways and in fluid communication with said radial passageways.

3. The catheter of claim 2 wherein the rotatable working head defines a generally planar surface that rotates above the circular groove in the bearing and extends radially outward to a sharp transition to an exposed portion of the working head spaced from the bearing by a small gap.

4. A catheter comprising:
 a) an elongated flexible sheath defining a center passageway and having a length to extend from outside a subject to a region of interest within a subject vessel;
 b) abrasion means comprising a distally located working head rotatably carried by the sheath for rotation with respect to the sheath and a drive member extending through the sheath's center passageway to apply motive power to the working head from a prime mover outside the subject; and
 c) a bearing rotatably supporting the working head and defining a bearing shaft portion which extends into a distal end of the flexible sheath and a bearing end portion that abuts a distal end of the sheath; said bearing shaft portion defining one or more axial fluid delivery passageways in fluid communication with a center passageway of said sheath that extend axially along the shaft portion of the bearing to the bearing end portion;
 d) said bearing end portion defining one or more radial passageways in fluid communication with said axial passageways that extend radially outward from regions continuously completely covered by the working head of said abrasion means through the bearing end portion to exposed regions of a distally facing end surface of the bearing end portion that open into the subject vessel.

5. The catheter of claim 4 wherein the end surface of the bearing end portion defines a circular groove radially outward of the radial passageways and in fluid communication with said radial passageways.

6. The catheter of claim 5 wherein the abrasion means defines a generally planar surface that rotates above the circular groove in the bearing and extends radially outward to a sharp transition with an exposed portion of the working head spaced from the bearing by a small gap.

7. A catheter for treating a subject vessel comprising:
a) an elongated flexible sheath having a center passageway and a length sufficient to extend from outside the subject to a treatment region within the subject vessel;
b) a rotatable working head supported at a distal end of said sheath for abrasively treating interior walls of the vessel as the working head rotates with respect to the sheath;
c) a drive shaft extending through the center passageway in the sheath and connected to the working head for transmitting motive power from outside the subject to the working head to effect rotation of the working head; and
d) a bearing carried by the sheath for rotatably supporting the working head; said bearing having a bearing body supported at a distal end of the flexible sheath which includes an annular portion and a flanged distal portion, said distal portion having a distally facing bearing end surface; said bearing body defining one or more fluid delivery passageways in fluid communication with a center passageway in the sheath which extend axially through the bearing body and extend radially outward from a region of the bearing covered by the working head through the flanged distal portion of the bearing body to open into the vessel via regions of the bearing end surface not covered by the working head;
e) said flanged portion of said bearing body defining a circular groove in the bearing end surface into which the fluid delivery passageways open.

8. The catheter of claim 7 wherein the rotatable working head defines a generally planar surface that rotates above the circular groove in the bearing and extends radially outward to a sharp transition to an exposed portion of the working head spaced from the bearing by a small gap.

* * * * *